United States Patent [19]
Thompson et al.

[11] Patent Number: 5,986,182
[45] Date of Patent: Nov. 16, 1999

[54] INBRED MAIZE LINE 4SQ601

[76] Inventors: Steven A. Thompson, 5326 Creekbend Dr., Carmel, Ind. 46033; Neil M. Cowen, 990 Tillson Dr., Zionsville, Ind. 46077

[21] Appl. No.: 08/942,055

[22] Filed: Oct. 1, 1997

[51] Int. Cl.$^6$ .............................. A01H 5/00; A01H 4/00; A01H 1/00; C12N 5/04

[52] U.S. Cl. ................ 800/320.1; 800/298; 800/275; 800/271; 435/412; 435/424; 435/430; 435/430.1

[58] Field of Search .............................. 800/320.1, 298, 800/275, 271; 435/412, 424, 432, 430.1

[56] References Cited

U.S. PATENT DOCUMENTS

| | | |
|---|---|---|
| 5,451,705 | 9/1995 | Larkins et al. . |
| 5,554,798 | 9/1996 | Lundquist et al. . |
| 5,589,605 | 12/1996 | Lindsey . |
| 5,608,139 | 3/1997 | Gogerty . |
| 5,608,140 | 3/1997 | Coaldrake et al. . |
| 5,618,987 | 4/1997 | Hoffbeck . |

OTHER PUBLICATIONS

Phillips et al. Cell/Tissue Culture and In Vitro Manipulation, In Corn and Corn Improvement ASA No. 18, 3rd edition, p. 358, 1987.

Alexander, D.E., "Breeding Special Nutritional and Industrial Types", *Corn and Corn Improvement*, pp. 869–880 (1988).

Alexander, D.E., "High Oil Corn: Breeding and Nutritional Properties" 43rd Annual Corn & Sorghum Research Conference, pp. 97–105.

Curtis, P.E., Leng, E.R., Hageman, R.H., "Developmental Changes in Oil and Fatty Acid Content of Maize Strains Varying in Oil Content", Crop Science, vol. 8, pp. 689–693 (Nov.–Dec. 1968).

Goldman, I.L., Rocheford, T.R., Dudley, J.W., "Molecular Markers Associated With Maize Kernel Oil Concentration in an Illinois High Protein + Illinois Low Protein Cross", *Crop Science*, vol. 34, pp. 908–915 (1994).

Miller, R.L., Dudley, J.W., Alexander, D.E., "High Intensity Selection for Percent Oil in Corn," *Crop Science,* vol. 21, pp. 433–435 (May–Jun. 1981).

Misevic, D., Maric, A., Alexander, D.E., Dumanovic, J., Ratkovic, S., "Population Cross Diallel Among High Oil Populations of Maize", *Crop Science,* vol. 29, pp. 613–617 (1989).

*Primary Examiner*—Gary Benzion
*Attorney, Agent, or Firm*—Woodard, Emhardt, Naughton, Moriarity & McNett Patent and Trademark Attorneys

[57] ABSTRACT

Inbred maize lines designated as 4SQ601 and 4SQ602, plants and seeds of such maize lines, methods for producing maize plants by crossing said lines with themselves or another maize plant, and hybrid maize seeds and plants produced by crossing said inbred maize lines with another maize line or plant.

11 Claims, 1 Drawing Sheet

INBRED MAIZE LINE 4SQ601

BACKGROUND OF THE INVENTION

1. Field of the Invention

The present invention relates generally to the production of maize, and more specifically to inbred maize lines designated 4SQ601 and 4SQ602, to parts thereof, and to maize plants produced using the same.

2. Description of the Related Art

As further background, maize, often referred to in the United States as corn, has long been the subject of plant breeding. Maize can be bred by self-pollination and cross-pollination techniques, both of which are typically employed in plant breeding programs with the object of combining a set of desired traits in a single maize hybrid.

Maize plants which have been self-pollinated and selected for type for several generations become homozygous at almost all gene loci. Such maize plants produce a uniform population of true breeding progeny, often referred to as an inbred maize line. In turn, these inbred maize lines are used primarily in cross-pollination with other inbred maize lines, to produce hybrid maize seed for commercial sale.

In general, the development of a hybrid maize variety involves three steps. Plants from germplasm pools or breeding populations are first selected. The selected plants are then self-pollinated, or "selfed", for several generations and selected to produce a series of true-breeding inbred lines differing from one another. Finally, the inbred lines are crossed with other inbred lines to produce hybrid progeny, ($F_1$).

It is known that during the maize inbreeding process, the vigor of the maize lines generally decreases. This vigor is then restored when two different inbred lines are crossed to produce the hybrid progeny ($F_1$). Importantly, a hybrid between a defined pair of inbred lines will always be the same, due to the homozygosity and homogeneity of the inbred lines utilized. Thus, hybrid maize seed can be sold to the market which yields a reliable, reproducible maize plant.

One maize trait of interest is kernel oil content. Standard maize grain typically contains about 3 to 4% oil on a dry weight basis. Maize grain having an elevated oil concentration, referred to as "high oil maize", has a higher caloric content per unit weight and is thus particularly advantageous for use as animal feed, and for its reduced dusting during milling. Because more than half of the maize grain produced in the United States is used for animal feed, the use of high oil maize for feed is of substantial commercial interest. This is particularly so in view of the high caloric demands in feeding poultry (*Gallus gallus domesticus*), swine (*Sus scrofa*), and dairy cows (*Bos taurus*). As it is, broiler and swine diets regularly contain added oil. Further, the full potential of bovine growth hormone in dairy cows will be more readily exploited if caloric intake is increased beyond that encountered with regular maize rations. Similar advantages may be expected in swine treated with porcine growth hormone.

Despite the expected advantages of high oil maize hybrids, the commercialization of high oil maize has been slow in progressing. This may be due to the fact that in several prior studies, breeding for high oil content has reduced yield both of inbreds and of hybrids made using the inbreds. Thus, competitive high-oil hybrids have proven difficult to develop.

In light of this background, a need exists for an inbred maize line having an elevated oil content and good combining ability with elite lines to produce competitive high oil maize hybrids. The present invention is addressed to this need.

SUMMARY OF THE INVENTION

According to the invention, there are provided high oil inbred maize lines designated 4SQ601 and 4SQ602. Thus, the present invention provides the seeds of inbred maize lines 4SQ601 and 4SQ602, the plants thereof, parts of such plants, and maize plants produced by self-pollinating such inbred lines or by crossing such inbred line with another maize line. The invention further provides hybrid maize seeds produced by crossing said inbred maize lines with another maize line, and the plants resulting therefrom and grain produced on them.

DESCRIPTION OF THE PREFERRED EMBODIMENT

Figure 1:
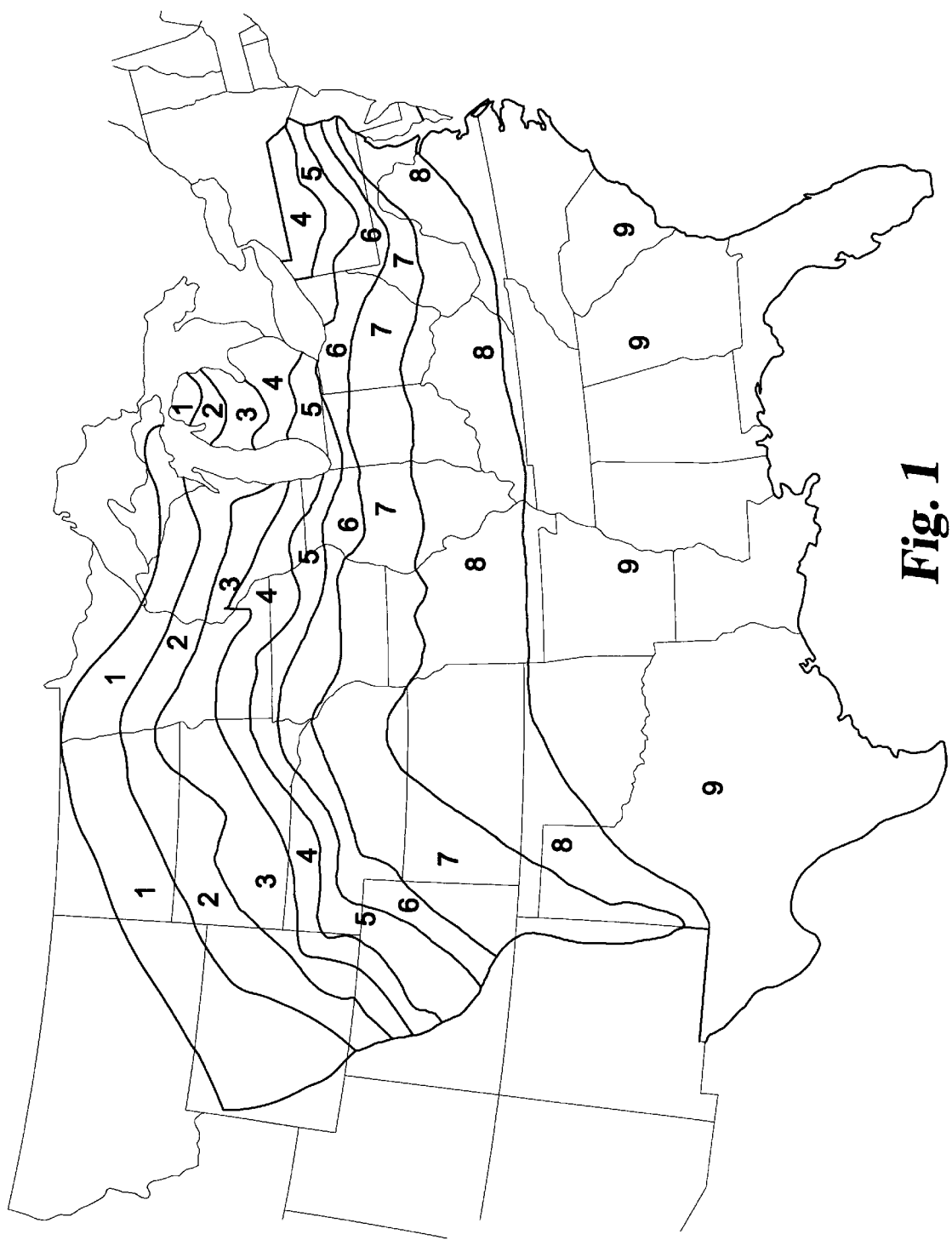
FIG. 1 shows the maturity zones for maize plants in the United States.

The present invention provides the seeds of inbred maize lines 4SQ601 and 4SQ602, the plants thereof, parts of such plants, and maize plants produced by self-pollinating such inbred lines or by crossing such inbred lines with another maize line. The invention further provides hybrid maize seeds produced by crossing said inbred maize lines with another maize line, and the plants resulting therefrom and grain produced on them.

As used herein, the term plant includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk and the like.

Inbred maize lines are typically developed for use in the production of hybrid maize lines. Inbred maize lines need to be highly homogeneous, homozygous and reproducible to be useful as parents of commercial hybrids. Many analytical methods are available to determine the homozygosity and phenotypic stability of these inbred lines.

The traditional analytical method is to observe phenotypic traits. The data are usually collected in field experiments over the life of the maize plants to be examined. Phenotypic characteristics most often observed include traits associated with plant morphology, ear and kernel morphology, insect and disease resistance, maturity, and yield.

Another trait which has been observed, particularly in the development of high oil maize, is kernel oil content. Such oil content has been measured using oil values both from composite samples and from single kernels. Silela et al., *Theor. Appl. Genet.*, 78: 298 (1989), demonstrated that the rate of oil content gain was significantly higher if breeding selection occurred on a single kernel basis. In such methods, single kernel values may be measured utilizing wide-line nuclear magnetic resonance (NMR) spectroscopy to non-destructively determine the oil content of a single maize kernel. Experiments reported by Alexander et al., *J. Am. Oil Chem. Soc.*, 44: 555 (1967), demonstrated a highly positive correlation between NMR and solvent-extracted oil content determinations in maize. As well, Orman et al., *J. Am. Oil Chem. Soc.*, 69: 1036–1038 (1992), demonstrated that near-infrared transmission spectroscopy (NITS) is useful to predict the oil content of single maize kernels. Accordingly, a variety of techniques such as these can be employed to observe kernel oil content in maize plants.

In addition to phenotypic observations, the genotype of a plant can also be examined. A variety of laboratory-based techniques are available for the characterization and comparison of plant genotypes as well. Among those commonly employed are Restriction Fragment Length Polymorphisms (RFLPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs).

Among these techniques, the most widely used are RFLPs and Isozyme Electrophoresis. These are discussed by Lee, M., "Inbred Lines of Maize and Their Molecular Markers", The Maize Handbook, (Springer-Verlag, New York, Inc. 1994, at 423–432), which is hereby incorporated herein by reference. RFLPs are capable of detecting an exceptionally high degree of allelic variation in maize plants, and there exist a large number of available markers. Isozyme Electrophoresis is useful for determining genetic composition, although the available number of markers and allelic variants is generally lower than that available using RFLPs.

Upon extensive observation, inbred maize lines 4SQ601 and 4SQ602 have shown uniformity and stability within the limits of environmental influence for typically assessed traits. The inbreds have been self-pollinated for a sufficient number of generations with careful attention paid to uniformity of plant type to ensure the homozygosity and phenotypic stability necessary for use in commercial production. No variant traits have been observed or are expected in 4SQ601 and 4SQ602.

Inbred maize lines 4SQ601 and 4SQ602 are yellow, dent maize inbreds exhibiting substantially the morphology of maize line CS405, the latter being subject of United States Plant Variety Protection Certificate No. 9200059 issued Mar. 31, 1993, except that 4SQ601 and 4SQ602 have a substantially elevated oil content compared to CS405. The morphologies of maize lines 4SQ601 and 4SQ602 are thus generally similar to maize lines having maize line B73 in their parentage. Maize lines 4SQ601 and 4SQ602 are high oil maize lines, and thus exhibit a kernel oil content greater than the 3–4% (dry weight basis) typically observed for most commercial hybrids. Although some variation may occur due to environmental and other like influences, inbred lines 4SQ601 and 4SQ602 typically have a kernel oil content of about 5–8% on a dry weight basis.

The pedigree for the maize lines of the invention includes the following. In 1992, two selfed ear samples were selected from a progeny designated 99B10306 for subsequent purification and selfing. These were designated as 99B10306.1 and 99B10306.2. They contained 6.8% and 7.0% oil, respectively, on a dry weight basis. In 1993, the two selfed ear samples selected from progeny 99B1306 were grown in Champaign, Ill., USA. Sample 99B10302.2 was selected for further purification and selfing, resulting ultimately in the two sublineages which form a part of the present invention, inbred maize lines 4SQ601 and 4SQ602.

In particular, a single ear, designated as 99B1306.21, was sampled. It contained 6.3% oil on a dry weight basis. In 1994, sample 99B10306.21 was grown in Champaign, Ill. and a single ear, designated 99B10306.211 was selected for further purification and testing. It contained 8.1% oil on a dry weight basis. Sample 99B10306.211 was grown in Champaign, Ill. in 1995. Two ears, designated as 99B10306.2111 and 99B10306.2112 were selected for further purification and selfing.

Samples 99B10306.2111 and 99B10306.2112 were grown in Molokai, Hi., USA in 1995/1996. 99B10306.2112 was selected for further purification. Two ears, designated as 99B10306.21121 and 99B10306.21122 were selected for further purification and testing. A sample from 99B10306.2 was also planted in Molokai, Hi. in 1995/1996. Six ears were selected for increase and designated as 99B10306.22-99B10306.27. In 1996, samples from 99B10306.21121 and 99B10306.21122 were grown in Champaign, Ill. for selfing. All ears conforming to the expected type were bulk shelled. This bulk sample, having an oil content of 6.7% on a dry weight basis, was designated as 4SQ601, and was used for increase. The six ears sampled from 99B10306.2 were planted in Champaign, Ill. for selfing and increase. All ears conforming to the expected morphological type were bulked and were designated as 4SQ602. This bulk, having an oil content of 6.6% on a dry weight basis, was also used for continued increase.

As indicated, maize RFLP linkage maps have been widely implemented in genotypic observations. RFLPs, genetic differences detectable by DNA fragment lengths, are usually detected by electrophoresis on agarose gel after digestion of the plant DNA with a restriction endonuclease. Restriction fragment length polymorphism analysis of DNA of sample 99B10306 of the pedigree of the inbred maize lines of the present invention was conducted as follows: DNA was prepared from lyophilized leaf tissue of 25 greenhouse-grown plants as described by Saghai-Maroof et al., *Proc. Natl. Acad. Sci USA* 81: 8014–8018 (1984). Eight micrograms of each DNA were digested with either EcoRI, HindIII or SstI as suggested by the manufacturer (Bethesda Research Laboratory, Gaithersburg, Md., USA) and separated by agarose-gel electrophoresis. The DNA was blotted onto nylon membranes as previously described (Southern, *J. Mol. Biol.* 98: 503 (1975); Southern, *Methods Enzymol.* 69: 152 (1980)).

Genomic and cDNA clones were selected from collections of mapped clones from Brookhaven National Laboratory, Upton, N.Y., USA, The University of Missouri, Columbia, Miss., USA, and CERES-NPI, Inc. (Salt Lake City, Utah, USA). Probe DNA was prepared using an oligo-labeling kit purchased from Pharmacia LKB Biotechnology, Inc. (Piscataway, N.J., USA) with 50 micro-Curies $^{32}$P-dCTP (3000 mCi/mM, NEN). Probes were hybridized to the DNA on the blots. Blots were then washed at 60° C. in 0.25×SSC and 0.2% SDS for 45 minutes, blotted dry, and exposed to XAR5 film overnight with two intensifying screens. The results are presented in Table 1.

TABLE 1

| Chromosomal location | Probe | Enzyme | Fixed | Segregating | Total number of fragments | Approximate size(s) (kb) of fragments detected | Parent 1 fragments | Parent 2 fragments |
|---|---|---|---|---|---|---|---|---|
| 1L | NPL 120 | SstI | X | | 1 | 6.3 | | |
| 1L | BNL 7.26 | EcoRI | | X | 2 | 20.5 | 5 | 20 |
| 1C | BNL 5.59 | EcoRI | X | | 2 | 20, 6.3 | | |
| 1C | NPL 272 | HindIII | X | | 3 | 14, 6.6, 4.4 | | |
| 1S | NPL 406 | HindIII | X | | 1 | 5 | | |
| 1S | NPL 234 | SstI | X | | 1 | 9 | | |
| 1S | NPL 415 | EcoRI | X | | 2 | 18,9.3 | | |
| 1S | NPL 453 | SstI | X | | 1 | 18 | | |
| 1S | UMC 157 | SstI | X | | 2 | 9.3, 4.4 | | |
| 2L | NPL 298 | SstI | X | | 1 | 16 | | |
| 2L | NPL 210 | SstI | | X | 3 | 18, 14, 6.6 | 16, 14 | 6.6 |
| 2L | NPL 610 | EcoRI | X | | 3 | 9.3, 8, 6.2 | | |
| 2C | NPL 297 | SstI | X | | 1 | 16 | | |
| 2C | NPL 356 | SstI | X | | 1 | 8 | | |
| 2S | NPL 402 | SstI | | X | 2 | 20, 18 | 18 | 20 |
| 2S | NPL 417 | SstI | | X | 2 | 7.5, 7 | 7.5 | 7.7 |
| 3L | NPL 296 | EcoRI | | X | 3 | 25, 12, 6.3 | 25, 6.3 | 12 |
| 3L | NPL 432 | EcoRI | X | | 1 | 18 | | |
| 3L | NPL 457 | SstI | X | | 1 | 9.3 | | |
| 3L | NPL 212 | EcoRI | X | | 1 | 6.6 | | |
| 3C | UMC 10 | EcoRI | X | | 1 | 7 | | |
| 3C | UMC 102 | EcoRI | X | | 1 | 4, 1.6 | | |
| 3S | BNL 8.15 | HindIII | X | | 1 | 18 | | |
| 3S | PNI 446 | SstI | X | | 1 | 7 | | |
| 3S | NPL 220 | HindIII | X | | 1 | 2.3 | | |
| 3S | UMC 121 | SstI | X | | 1 | 9.3 | | |
| 4L | NPL 333 | HindIII | X | | 2 | 10.6 | | |
| 4L | NPL 270 | SstI | X | | 1 | 3 | | |
| 4C | NPL 396 | HindIII | X | | 2 | 11, 9.3 | | |
| 4C | UMC 19 | HindIII | X | | 1 | 4.4 | | |
| 4S | UMC 31 | SstI | | X | 2 | 8.4 | | |
| 4S | NPL 386 | HindIII | X | | 1 | 9.3 | | |
| 4S | NPI 386 | HindIII | X | | 1 | 9.3 | | |
| 4S | UMC 87 | SstI | | X | 2 | 8, 4.2 | 8 | 4.2 |
| 5L | NPI 408 | EcoRI | | X | 3 | 9.3, 4.8, 4.5 | 9.3, 4.8 | 4.5 |
| SL | UMC 128 | HindIII | | X | 3 | 23, 6.8, 2 | 23, 6.8 | 2 |
| 5C | NPI 295 | SstI | X | | 1 | 9.3 | | |
| 5S | NPI 409 | HindIII | X | | 1 | 7 | | |
| 5S | UMC 43 | HindIII | X | | 1 | 3 | | |
| 6L | NPI 223 | SstI | | X | 2 | 12, 10 | 10 | 12 |
| 6L | NPI 252 | SstI | | X | 2 | 14, 4.4 | 4.4 | 14 |
| 6L | NPI 280 | EcoRI | | X | 2 | 25, 8 | 8 | 25 |
| 6L | NPI 581 | HindIII | | X | 3 | 16, 14, 6.6 | 14 | 16, 6.6 |
| 6L | UMC 85 | EcoRI | | X | 2 | 14, 8.5 | 14 | 8.5 |
| 6C | NPI 373 | EcoRI | | X | 2 | 7,4 | 7 | 4 |
| 6S | NPI 377 | HindIII | | X | 4 | 12, 10, 5.5, 4.4 | 12, 10 | 5.5, 4.4 |
| 6S | NPI 606 | SstI | X | | 2 | 12, 4 | | |
| 7L | NPI 455 | SstI | X | | 1 | 3.5 | | |
| 7L | NPI 263 | EcoRI | X | | 1 | 7 | | |
| 7L | NPI 433 | HindIII | X | | 4 | 12, 10, 7, 4 | | |
| 7L | NPI 433 | HindIII | X | | | 12, 10, 7, 4 | | |
| 7C | NPI 430 | SstI | X | | 3 | 18, 9, 8 | | |
| 8L | UMC 48-7 | HindIII | X | | 1 | 2.1 | | |
| 8L | UMC 48-7 | HindIII | X | | 1 | 2.1 | | |
| 8L | NPI 268 | SstI | X | | 1 | | | |
| 8L | NPI 107 | SstI | X | | 2 | 14, 9.3 | | |
| 8L | NPI 595 | SstI | | X | 2 | 8, 7.5 | 8 | 75 |
| 8L | UMC 12 | SstI | X | | 1 | 14 | | |
| 8C | NPI 585 | HindIII | | X | 2 | 12, 6.6 | 6.6 | 12 |
| 8S | NPI 110 | EcoRI | | X | 2 | 25, 10 | 25 | 10 |
| 9S | NPI 211 | HindIII | | X | 2 | 9, 1.5 | 1.5 | 9 |
| 9S | NIP 266 | SstI | | X | 2 | 20, 18 | 18 | 20 |
| 10L | NIP 264 | EcoRI | X | | 2 | 18, 9.3 | | |
| 10L | NPI 264 | EcoRI | | X | 2 | 18, 9.3 | 18 | 9.3 |
| 10L | NPI 563 | HindIII | | X | 2 | 5, 4.4 | 5 | 4.4 |
| 10C | NPI 105 | HindIII | X | | 7 | 18, 11, 10, 6.6, 4.8, 3.8, 3.4 | | |

As can be seen, segregation as some of the tested markers was exhibited in 99B10306. Due to further purification and selfing, it is expected that maize lines 4SQ601 and 4SQ602 are fixed at all or essentially all markers shown in Table 1.

The present invention also is directed to methods for producing a maize plant by crossing a first parent maize plant with at least a second parent maize plant, wherein the first or second parent maize plant is an inbred maize plant of the line 4SQ601 or 4SQ602. Further, both first and second parent maize plants can come from the inbred maize line 4SQ601 and/or 4SQ602. Thus, any such methods using the inbred maize line 4SQ601 and/or 4SQ602 are part of this invention: selfing, backcrosses, hybrid production, crosses to populations, and the like, are included. All plants produced using inbred maize line 4SQ601 and/or 4SQ602 as parent(s) are also within the scope of this invention. Advantageously, the inbred maize lines are used in crosses with other, different, maize inbreds to produce first generation ($F_1$) maize hybrid seeds and plants with superior characteristics.

In any cross, one of the parental lines involved may be preferred as the male and the other as the female, considering the phenotypic characteristics of the parental plants which affect reproduction. As illustrations, one of the parental lines may have a higher seed yield, one may shed pollen more advantageously, and one may have more desirable tassel or seed characteristics. Maize lines 4SQ601 and 4SQ602 are suited as either males or a females in crosses for producing first generation $F_1$ maize hybrids, and are best suited as females. Inbred maize lines 4SQ601 and 4SQ602 are best adapted to the central Corn Belt of the United States, approximately maturity zones 4–7 shown in FIG. 1 (best in zones 5–6), and are best used to produce hybrids of the same growth adaptation.

Inbred maize lines 4SQ601 and 4SQ602 exhibit surprisingly good combining ability with elite maize lines to produce competitive, high oil hybrids ($F_1$). For example, inbred maize lines 4SQ601 and 4SQ602 combine well with proprietary elite line CQ715 of Mycogen Seeds, Minneapolis, Minn., USA, to produce a high oil maize hybrid. For example, inbred maize line 4SQ601 has been crossed with CQ715 to result in a hybrid maize plant having the characteristics shown in Table 2, comparing favorably to the other elite hybrids shown (abbreviations: bu/a=bushels per acre; lbs/a=pounds per acre)

TABLE 2

| Maize | Yield (bu/a) | % $H_2O$ | % Protein | % Oil | Protein (lbs/a) | Oil (lbs/a) |
|---|---|---|---|---|---|---|
| 4SQ601 x CQ715 | 162.7 | 21.8 | 12.9 | 6.1 | 1002 | 474 |
| Brand 2616* | 161.7 | 21.6 | 11.6 | 4.2 | 896 | 326 |
| Brand 2636* | 160.6 | 21.6 | 12.4 | 3.9 | 944 | 297 |
| Brand 2689* | 168.3 | 22.3 | 10.7 | 4.0 | 858 | 320 |
| Brand 2677* | 169.7 | 22.6 | 11.3 | 4.1 | 912 | 333 |

*Maize brands commercially available from Mycogen Seeds, Minneapolis, Minnesota, USA.

Thus, the hybrid 4SQ601×CQ715 is a highly competitive yielding, high oil and high protein maize plant.

Inbred maize lines 4SQ601 and 4SQ602, being substantially homozygous, can be reproduced by planting seeds of the line, growing the resulting maize plants under self-pollinating or sib-pollinating conditions with adequate isolation, and harvesting the resulting seed, using techniques familiar to the agricultural arts.

In another aspect of the invention, maize plants may also be regenerated from cells in culture (Gordon-Kamm et al., Transformation of Maize Cells and Regeneration of Fertile Transgenic Plants," *The Plant Cell*, V.2, 603–618 (1990), herein incorporated by reference). For such regeneration, somatic cells from a 4SQ601 or 4SQ602 plant may be obtained and cultured in vitro in a medium comprising an embryogenic-promoting hormone to result in callus organization. Such agents may include, for example, dicamba, 2,4-D, and the like. The cells are then transferred to a medium which includes a tissue organization-promoting hormone such as BAP, myoinositol, 2,4-D, ABA, NAA, IAA and/or 2IP. After observation of tissue organization, the cells can be subcultured onto a medium without the hormone to allow for shoot elongation or root development, for example stimulated by IBA. Finally, the resulting plantlets can be transferred to a minimal medium to provide for hardening of the plant. Such minimal medium may be, for example, Clark's media.

Maize tissue culture procedures are also described in Green and Rhodes, "Plant Regeneration in Tissue Culture of Maize", *Maize for Biological Research* (Plant Molecular Biology Association, Charlottesville, Va. 1982, at 367–372) and in Duncan, et al., "The Production of Callus Capable of Plant Regeneration from Immature Embryos of Numerous Zea Mays Genotypes", 165 *Planta* 322–332 (1985), each of which is also hereby incorporated herein by reference. Thus, it is clear from the literature that the state of the art is such that regenerative methods of obtaining plants are routinely used, and such methods as applied using cells of inbred line 4SQ601 or 4SQ602 also form a part of the present invention.

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have applications in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seeds of inbred maize line 4SQ601 and 4SQ602, the plants produced from the inbred seeds, the hybrid maize plants produced from the crossing of the inbreds, hybrid seeds, and various parts of the hybrid maize plants can be utilized for human food, livestock feed, and as raw materials in industry.

Applicants have made deposits of at least 2500 seeds of Inbred Corn Lines 4SQ601 and 4SQ602 with the American Type Culture Collection (ATCC), Rockville, Md. 20852 U.S.A., ATCC Deposit Nos. 209315 (corresponding to 4SQ601) and 209316 (corresponding to 4SQ602). The seeds were deposited with the ATCC on Oct. 1, 1997 and were taken from samples maintained by Mycogen Seeds, Minneapolis, Minn., USA from a date prior to the filing date of this application. The deposits of the Inbred Corn Lines 4SQ601 and 4SQ602 will be maintained in the ATCC depository, which is a public depository, for a period of 30 years, or 5 years after the most recent request, or for the enforceable life of the patent, whichever is longer; and will be replaced if it becomes nonviable during that period.

Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 U.S.C. 2321 et seq.).

The foregoing invention has been described in detail by way of illustration and example for purposes of clarity and understanding. However, it will be readily apparent to those in the field that certain changes and modifications such as single gene modifications and mutations, somoclonal variants, variant individuals selected from large populations of the plants of the present inbreds and the like may be practiced within the scope of the invention, as limited only by the scope of the appended claims.

What is claimed is:

1. Seeds of inbred maize line designated 4SQ601 and having ATCC Accession No. 209315.
2. A maize plant produced by the seeds of claim 1, or its parts.
3. Pollen of the plant of claim 2.
4. An ovule of the plant of claim 2.
5. A maize plant having all the physiological and morphological characteristics of the maize plant designated 4SQ601, the seeds of which have been deposited under ATCC Accession No. 209315.
6. A method for producing first generation hybrid maize seed, comprising crossing a first inbred parent maize plant with at least a second inbred parent maize plant, and harvesting the resultant first generation hybrid maize seed, wherein said first or second parent maize plant is the maize plant of claim 2.
7. The method of claim 6 wherein inbred maize plant 4SQ601, the seeds of which have been deposited under ATCC Accession No. 209315, is the female parent.
8. The method of claim 6 wherein inbred maize plant 4SQ601, the seeds of which have been deposited under ATCC Accession No. 209315, is the male parent.
9. An $F_1$ hybrid seed produced by crossing an inbred maize plant according to claim 2 with another, different maize plant.
10. An $F_1$ hybrid plant grown from the seed of claim 9, or its parts.
11. A cell which upon growth and differentiation produces a maize plant having all the physiological and morphological characteristics of the maize plant designated 4SQ601, the seeds of which have been deposited under ATCC Accession No. 209315.

* * * * *